(12) United States Patent
Miller-Podraza et al.

(10) Patent No.: US 7,902,170 B2
(45) Date of Patent: Mar. 8, 2011

(54) INFLUENZA VIRUS BINDING, SIALYLATED OLIGOSACCHARIDE SUBSTANCE AND USE THEREOF

(75) Inventors: Halina Miller-Podraza, Västra Frölunda (SE); Karl-Anders Karlsson, Göteborg (SE)

(73) Assignee: Biotie Theraples Corp., Turku (FI)

( * ) Notice: Subject to any disclaimer, the term of this patent is extended or adjusted under 35 U.S.C. 154(b) by 156 days.

(21) Appl. No.: 10/311,713

(22) PCT Filed: Jun. 20, 2001

(86) PCT No.: PCT/FI01/00587
§ 371 (c)(1),
(2), (4) Date: May 21, 2003

(87) PCT Pub. No.: WO01/97819
PCT Pub. Date: Dec. 27, 2001

(65) Prior Publication Data
US 2003/0181714 A1    Sep. 25, 2003

(30) Foreign Application Priority Data
Jun. 21, 2000  (FI) .................................. 20001477

(51) Int. Cl.
*A61K 31/715* (2006.01)
*A61K 31/739* (2006.01)
*C07H 5/04* (2006.01)
(52) U.S. Cl. .......... 514/54; 536/55.1; 536/53; 536/123.1
(58) Field of Classification Search ................. 536/55.1; 514/54; 536/53, 123.1
See application file for complete search history.

(56) References Cited

U.S. PATENT DOCUMENTS 5,101,026 A * 3/1992 Ogawa et al.
5,220,008 A   6/1993 Sabesan
5,254,676 A   10/1993 Sabesan
5,736,533 A * 4/1998 Simon et al. .................... 514/61
6,132,994 A * 10/2000 Tawada et al. ................. 435/84

OTHER PUBLICATIONS

Natunen et al. (FEBS Letters 452 (1999) 272-276).*
Sabesan et al. (Journal of American chemical society (1991), 113(15), 5865-6).*
Natunen et al. (FEBS Letters 452 (1999) 272-276) (abstract sent, the abstract is from STN, Accession No. 1999:424946 CAPLUS, Document No. 131:226463).*
Sabesian et al. (Journal of American Chemical Society, 1991, 113, 5865-5866).*
Suzuki, Prog. Lipid Res., vol. 33, No. 4, pp. 429-457 (1994).
Laver et al., Scientifiv American, vol. 280, No. 1, pp. 78-97 (1999).
A. S. Gambaryan et al., *FEBS Letters*, vol. 366, pp. 57-60 (1995).
M. Matrosovich et al., *Virology*, vol. 223, pp. 413-416, Article No. 0498 (1996).
J. Müthing, *Carbohydrate Research*, vol. 290, pp. 217-224 (1996).
J. Müthing et al., *Glycoconjugate Journal*, vol. 10, pp. 120-126 (1993).
Y. Suzuki et al., *J. Biol. Chem.*, vol. 261, No. 36, pp. 17057-17061 (Dec. 25, 1986).
Y. Suzuki et al., *Biochimica et Biophysica Acta*, vol. 903, pp. 417-424 (1987).
Y. Suzuki et al., *Virology*, vol. 189, pp. 121-131 (1992).
S. Sabesan et al., *J. Am. Chem. Soc.*, vol. 114, 8363-8375 (1992).

* cited by examiner

*Primary Examiner* — Shaojia Anna Jiang
*Assistant Examiner* — Michael C Henry
(74) *Attorney, Agent, or Firm* — Birch, Stewart, Kolasch and Birch, LLP (57) ABSTRACT

The present invention is directed to human influenza virus binding substance containing at least one oligosaccharide chain, which comprises a terminal NeuNAcα6 linked to: (a) a linear or branched polylactosamine type structure consisting of at least three lactosamine residues, a linear sequence optionally containing one or two α3-linked fucose residues in a non-sialylated lactosamine, a branched structure optionally carrying one or more additional NeuNAcα-residues at a terminal position in a branch, and/or (b) a linear or branched structure with two lactosamine and one lactose residue, a linear structure in addition containing one or two α3-linked fucose residues in a non-sialylated lactosamine or lactose, a branched structure optionally carrying one additional NeuNAcα-residue in a terminal position of the branch, or an analog or derivative of said oligosaccharide chain for use in binding of human influenza virus.

10 Claims, 8 Drawing Sheets

INFLUENZA VIRUS BINDING, SIALYLATED OLIGOSACCHARIDE SUBSTANCE AND USE THEREOF

This application is the national phase under 35 U.S.C. §371 of PCT International Application No. PCT/FI01/00587 which has an International filing date of Jun. 20, 2001, which designated the United States of America.

FIELD OF THE INVENTION

The present invention relates to a substance or a receptor binding to human influenza virus, as well as use thereof in pharmaceutical compositions and a method for treatment of a condition due to the presence of influenza virus in the human respiratory tract. The invention is also directed to the use of the receptor for diagnostics of influenza viruses.

BACKGROUND OF THE INVENTION

Influenza virus attachment to host cells is mediated by specific interactions of the viral envelope protein hemagglutinin (HA) with sialylated carbohydrate chains of cell surface glycoproteins and glycolipids (for reviews, Suzuki, 1994; Herrler et al., 1995; Paulson, 1985; Wiley and Skehel, 1987). Natural sialylglycoproteins and gangliosides exhibit significant structural diversity, and different receptors are probably utilized by the viruses in different host tissues. It has been shown, that influenza A viruses isolated from avian species preferentially bind to NeuAcα3Gal-terminated sugar chains, while closely related human viruses reveal a higher binding affinity towards the NeuAcα6Gal-terminated structures (Paulson, 1985; Suzuki, 1994; Connor et al., 1994; Matrosovich et al., 1997; Gambaryan et al, 1997). Additional influential features for binding are inner parts of saccharide chains (Gambaryan et al., 1995; Matrosovich et al., 1997; Rogers and Paulson, 1983; Suzuki et al., 1987; Suzuki et al., 1992; Eisen et al., 1997), polyvalency of receptor saccharides (Pritchett and Paulson, 1989; Matrosovich, 1989; Mammen et al., 1995), spatial arrangement of sialyloligosaccharides in receptor glycoproteins (Pritchett and Paulson, 1989), or glycosylation of the viral hemagglutinins (Gambaryan et al., 1998; Ohuchi et al., 1997). Detailed molecular mechanisms of these effects and the importance of a variation in fine structure of sialylated receptors for the virulence and pathogenicity of individual viral strains are not known. For example virulence of the 1918 influenza pandemic still remains unexplained (Laver et al., 1999), and the actual strains have not been assayed for receptor specificity.

Studies on the structural characterization of biological receptors for human influenza viruses are hampered by the limited availability of the human respiratory tract tissues. However, characterization of the binding molecules from other human tissues may permit further specification of the receptor binding epitopes. Human leukocytes represent an attractive experimental model because they contain a series of gangliosides with high binding affinity for the virus. Binding species were detected in human leukocytes among common gangliosides (Müthing et al. 1993; Müthing, 1996). In contrast to the present invention these were described to contain α3-sialylated sialyl-Lewis x and VIM-2 sequences. The receptor activity was also observed among highly complex glycolipid fractions, polyglycosylceramides (Matrosovich et al., 1996). NeuAcα6-containing glycolipids of human leukocytes with more than two lactosamine units in the core chain have not yet been characterized by other laboratories (Müthing et al., 1993; Müthing et al. 1996; Müthing, 1996; Stroud et al., 1995; Stroud et al., 1996). They occur in human white cells in very small amounts and their existence has so far been neglected. However, these minor species may be of biological importance for in vivo events during influenza infections and may explain virulence variations between strains (Laver et al., 1999).

Binding of influenza viruses to sialic acid-containing neutrophil receptor(s) depresses bactericidal activity of neutrophils (Abramson and Mills, 1988; Cassidy et al., 1989; Daigneault et al., 1992; Abramson and Hudnor, 1995) and stimulates apoptosis of these cells by a yet undefined mechanism (Colamussi et al., 1999). This virus-mediated neutrophil dysfunction is a likely contributor to the development of secondary bacterial infections, which are the main cause of morbidity and mortality during influenza epidemics.

Several studies describe sialylated di- to heptasaccharide binding structures for human influenza viruses e.g. (Gambaryan et al., 1995; Matrosovich et al., 1997; Rogers and Paulson, 1983; Suzuki et al., 1992; Eisen et al., 1997). These have low affinities to the viruses and the studies do not describe larger saccharide receptors which have the high natural binding affinity. The divalent NeuNAcα6Galβ4GlcNAc-saccharides constructed chemically on β-galactosides are described in Sabesan, S. et al. -92 and in U.S. Pat. Nos. 5,254,676 and 5,220,008 and have only modestly better affinities than corresponding monosialocompounds even when linked on bovine serum albumin in multivalent form.

Several synthetic polymeric influenza inhibitors containing sialic acid (Mammen et al., 1995) or sialylated lactose/N-acetyllactosamine have been described (Gambaryan et al, 1997). The specific binding of human influenza virus to NeuNAcα6Galβ4GlcNAc-epitopes (Gambaryan et al, 1997) and the presence of NeuNAcα6Gal on the surface of human-ciliated tracheal epithelium (Baum and Paulson, 1990) were suggested to constitute an essential part of the biologically relevant cellular receptor for the viruses (Gambaryan et al, 1997).

A polylactosamine containing and α6-sialylated inhibitor of human influenza viruses has been described. This molecule is produced from a cryptically I-active (anti-I-antibodies are known to recognize polylactosamine and non-polylactosamine structures) glycoprotein 2 of bovine erythrocytes by removing sialic acid residues by sialidase treatment and by enzymatic resialylation by α3- or α6-sialyltransferases (Suzuki et al., 1987). The semisynthetic bovine protein is not a natural receptor structure of human viruses. It is hardly useful as a therapeutic inhibitor of human influenza viruses, because it contains a protein structure and a substantial amount of Galα3Galβ4GlcNAc-xeno-antigenic structures (Suzuki et al, 1985). The Galα3Galβ4GlcNAc-antigen is present in many mammalian species but not produced by human tissues, the structure is highly antigenic in human, and there are naturally large amounts of antibodies against the structure in humans. Foreign protein structures are known to be potential antigens and allergens for humans.

The authors (Suzuki et al., 1987) discuss that inner I-active neolacto-series type II sugar chains may also be important as a common part of the receptor determinant toward the hemagglutinin of human influenza viruses A and B. Unfortunately their saccharide material is very heterogenous and the possible sialylated I-active components formed were not characterized chemically and no specific epitopes were assigned as virus binding structures. According to the data of FIG. 3 corresponding to oligosaccharides labelled at the reducing end, the large I-polylactosamines are actually very minor species in the glycoprotein II and smaller O-glycans are major species in molar amount, the smaller O-glycans without branched polylactosamime are also recognized by at least one anti-I-antibody used to determine the saccharides of the protein (Suzuki et al., 1985). In another study the same authors show that α3-sialylated and α3-galactosylated branched polylactosamine glycolipid (also an I-antigenic structure) was shown to be a binding compound for influenza virus (Suzuki et al., 1986).

DETAILED DESCRIPTION OF THE INVENTION

In the invention, the binding of human viruses to gangliosides from different human tissues and cells, including leukocytes, was studied. The human virus bound selectively to only minor extended ganglioside species. So far other laboratories have not been able to detect and isolate the minor active species containing NeuNAcα6 sequences even when starting with huge amounts of leukocytes. The combination of the older and newly developed special overlay techniques used by the inventors together with the most sensitive mass spectrometry experiments allowed analysis of the novel receptors for human influenza virus.

Sialyl-Lewis x and VIM-2-active saccharides were excluded as parts of the active receptors binding the human influenza virus. Human is known not to contain Galα3-structures Larsen et al, 1990). It was also shown using SNA lectin that the binding was to some minor NeuNAcα6-containing species. In addition, it was demonstrated, that the binding was dependent on the presence of the unchanged glycerol sialic acid tail. The monosaccharide and ceramide compositions of the smallest active molecules were indicated by mass spectrometric data of the active fraction. Mass spectrometry data together with the other evidence allowed us to describe further potential structural features present in the high affinity species. Assignments are based on the knowledge that the $HexNAc_xHex_{x+2}$ in the glycolipid fractions correspond to polylactosamine sequences. The structural features described are in accordance with the previously known glycolipid structures of human leukocytes (Stroud et al., 1995; Stroud et al., 1996; Stroud et al., 1996b; Müthing, 1996, Johansson and Miller-Podraza, 1998) except for the presence α6-linked sialic acid on the structures.

The invention first describes the minimum structural elements present in the high affinity receptor of human influenza virus. The receptor active species contain at least one oligosaccharide chain, which comprises a terminal NeuNAcα6 linked to (a) -a linear or branched polylactosamine type structure consisting of at least three lactosamine residues, a linear sequence optionally containing one or two α3-linked fucose residues in a non-sialylated lactosamine, a branched structure optionally carrying one or more additional NeuNAcα-residues at a terminal position in a branch, and/or (b) -a linear or branched structure with two lactosamine and one lactose residue, a linear structure in addition containing one or two α3-linked fucose residues in a non-sialylated lactoseamine or lactose, a branched structure optionally carrying one additional NeuNAcα-residue in a terminal position of the branch. These active receptor epitopes are called virus binding structures.

The virus binding substances contain no Galα3Galβ4GlcNAc-residues as active virus binding parts and is preferably not linked to a protein and preferably do not contain any Galα3Galβ4GlcNAc-xenoantigenic structures. The virus binding substances are preferentially presented in clustered form such as by glycolipids on cell membranes, micelles, liposomes or on solid phases such as TCL-plates used in the assays. The clustered representation with correct spacing creates high affinity binding. According to a preferred embodiment the virus binding substance thus contains at least two oligosaccharides as defined, preferably at least three or at least four oligosaccharides as defined. It is noted from the TLC-assays that larger polylactosamine type compounds containing the NeuNAcα6-terminal are also receptor for the viruses. These compounds present in even more minor amounts are very high affinity receptors for the virus. Repeating virus binding epitopes containing branches with NeuNAcα6Galβ4GlcNAc on larger polylactosamine structures can effectively bind to several binding sites of virus surfaces, most probably on the hemagglutinin protein. The large glycolipid fraction is continuous with larger molecular weight polylactosamine glycolipid fraction called polyglycosylceramides. It has been recently shown that the polyglycosylceramide fraction has very high affinity for human influenza virus (Matrosovich et. al, 1996) and in a separate study these polylactosamines have been shown to carry NeuNAcα6-terminal structures (Johansson and Miller-Podraza, 1998). In a preferred embodiment the virus binding substances are presented on polylactosamine-type oligo- or polysaccharide or glycosides thereof. In the middle and non-reducing terminal parts of natural virus binding polylactosamines the binding epitope does not contain lactose residues, but a lactose residue may be present at the reducing end.

According to the invention it is possible to use the influenza virus binding epitopes or naturally occurring or a synthetically produced analogue or derivative thereof having a similar or better binding activity with regards to human influenza virus. It is also possible to use a substance containing the virus binding substance, such as a receptor active polylactosamine ganglioside described in the invention or an analogue or derivative thereof having a similar or better binding activity with regards to human influenza virus.

The virus binding substance may be a glycosidically linked terminal epitope of an oligosaccharide chain. Alternatively the virus binding epitope may be a branch of a polylactosamine chain.

Further assignment of the most potential receptor structures is possible based on the following facts. The SNA-lectin recognizes the terminal NeuNAcα6Gal-sequence. The presence of two NeuNAcs with α6 or α3-linkages indicates that the N-acetyllactosamine structures are branched. The biosynthetic knowledge in the art indicates that terminal NeuNAcα6Galβ4GlcNAc sequences are not α3 fucosylated (e.g. Paulson et al, 1978; DeVries et al, 1995), indicating that fucose residues are located further away from terminal Neu-NAc as in NeuNAcα6Galβ4GlcNAcβ3Galβ4(Fucα3) GlcNAcβ. Branching and fucosylation are exclusive on the same N-acetyllactosamine sequence of the known leucocyte type enzymes (Niemelä et al., 1998; Mattila et al., 1998). Furthermore, the Glc-residue is not fucosylated by the major fucosyltransferase of leukocytes (De Vries et al., 1995; Clarke and Watkins, 1996), which is in accordance with the knowledge of the vast majority of the isolated human oligosaccharide structures. However, the analysis does not exclude the presence of other minor isomeric species which are synthesized by yet uncharacterized biosynthetic reactions. Under the assay conditions described, the linear chain glycolipids NeuNAcα6Galα4GlcNAcβ3Galβ4GlcβCer or NeuNAcα6Galβ4GlcNAcβ3Galβ4GlcNAcβ3Galβ4GlcβCer did not show binding, indicating specific structural features on the larger binding glycolipids.

Mass spectrometry indicated the presence of disialylated and/or difucosylated molecules in the active fraction with an abundance of the active species, disialylation and difucosylation being structural features different from the non-active linear sequences. The disialylated species matches most correctly to the molecular masses of the saccharide sequences with the same lipid species previously known to be present in major sialylated glycolipids of leukocytes. These data indicate that the disialylated and/or difucosylated species belong to the high affinity receptor species.

The saccharide sequences of the receptor disialylated molecules are according to the experimental evidence and current biosynthetic and structural knowledge: NeuNAcα6Galβ4GlcNAcβ3(NeuNAcα6/or 3Galβ4GlcNAcβ6)Galβ4GlcNAcβ-3Galβ4GlcβCer and NeuNAcα6Galβ4GlcNAcβ3(NeuNAcα6/or 3Galβ4GlcNAcβ6)Galβ-4GlcβCer. The lectin binding assays indicate that most of the active species are devoid of NeuNAcα3, therefore indicating species having both branches with NeuNAcα6: NeuNAcα6Galβ4GlcNAcβ3 (NeuNAcα6Galβ4GlcNAcβ6) Galβ4GlcNAcβ3Galβ4GlcβCer and NeuNAcα6Galβ4GlcNAcβ3(NeuNAcα6Galβ4GlcNAcβ6) Galβ4GlcβCer. The binding of the more elongated decasaccharide sequences to the influenza virus may be more effective. The similar terminal octasaccharide sequences are defined as virus binding substances. The preferred disialylated virus binding substances have the structures: NeuNAcα6Galβ4GlcNAcβ3(NeuNAcα6/or 3Galβ4GlcNAcβ6)Galβ4GlcNAc, NeuNAcα6Galβ4GlcNAcβ3(NeuNAcα6/or 3Galβ4GlcNAcβ6)Galβ4Glc, NeuNAcα6Galβ4GlcNAcβ3 (NeuNAcα6Galβ4GlcNAcβ6)Galβ4GlcNAc, and NeuNAcα6Galβ4GlcNAcβ3(NeuNAcα6Galβ4GlcNAcβ6) Galβ4Glc.

The saccharide sequences of the receptor difucosylated molecules are according to the experimental evidence and current biosynthetic and structural knowledge: NeuNAcα6Galβ4GlcNAcβ3Galβ4(Fucα3) GlcNAcβ3Galβ4(Fucα3)GlcNAcβ3Galβ4Glcβ-Cer and a less likely form of fucosylated lactose: NeuNAcα6Galβ4GlcNAcβ3Galβ4(Fucα3) GlcNAcβ3Galβ4(Fucα3)GlcβCer, the saccharide sequence of this is considered as an effective analog of the terminal nonasaccharide sequence of the longer version. The specific structural feature of difucosylation together with NeuNAcα6 is considered to be active part in the recognition of the virus. Preferentially the difucosylated virus binding structures are NeuNAcα6Galβ4GlcNAcβ3Galβ4(Fucα3) GlcNAcβ3Galβ4(Fucα3)GlcNAc and NeuNAcα6Galβ4GlcNAcβ3Galβ4(Fucα3) GlcNAcβ3Galβ4(Fucα3)Glc.

A further extension of the glycolipid could be a structural feature increasing the receptor activity in comparison to the non-active species. Mass spectrometry peaks indicating the presence of the major non-receptor active α3-sialylated species, may also contain signals corresponding to isomeric α6-sialylated molecules. The extended receptors have structures NeuNAcα6Galβ4GlcNAcβ3Galβ4(Fucα3)$_{0-1}$GlcNAcβ3Galβ4(Fucα3)$_{0-1}$ GlcNAcβ3Galβ4GlcβCer, where the molecule has 0 or 1 fucosyl residues. Furthermore a branched monosialylated structure is possible with the same molecular weight as the linear non-sialylated forms such as NeuNAcα6Galβ4GlcNAcβ3(Galβ4GlcNAcβ6)-Galβ4GlcNAcβ3Galβ4GlcβCer. The extended linear and branched structural features are very similar to the species indicated above and therefore these molecules are likely to also have receptor activity. The sequences NeuNAcα6Galβ4GlcNAcβ3Galβ4(Fucα3)$_{0-1}$GlcNAcβ3Galβ4(Fucα3)$_{0-1}$GlcNAc, where the molecule has 0 or 1 fucosyl residues and NeuNAcα6Galβ4GlcNAcβ3(Galβ4GlcNAcα6)Galβ4GlcNAc are also virus binding structures.

When present as a branch of a longer polylactosamine chain the virus binding substance has the structure R-3 or 6Galβ4GlcNAcβ6/3(NeuNAcα6Galβ4GlcNAcβ3/6)Galβ-4GlcNAcβ4R$_2$, where the R is a glycosidically linked non-reducing end part of the polylactosamine, and R$_2$ is glycosidically linked to the reducing end part of the polylactosamine chain, preferably the R and/or R$_2$ contain more virus binding substances. The reducing end of the saccharide may be further derivatized.

The oligosaccharide chain of the invention can be a part of a polylactosamine chain or a conjugate thereof. Preferably, the polylactosamine chain contains at least 6 lactosamine residues or at least three sialic acid residues.

The virus binding substances may be conjugated to a carrier. The conjugation is performed by inking the virus binding substance preferably from the reducing end to a carrier molecule. When the conjugate is used in therapeutics, the carrier molecule is preferably not a protein.

The virus binding substances, preferably in oligovalent or clustered form, can be used to treat a disease or condition caused by the presence of the influenza virus in the respiratory tract of a patient. In such case the substances of the invention are used for anti-adhesion, i.e. to inhibit the binding of human influenza viruses to the receptor epitopes of the target cells or tissues. The target cells are neutrophils or epithelial cells of the respiratory tract. When the substance or pharmaceutical composition according to the invention is administered it will compete with the receptor glycoconjugates on the target cells for the binding of the viruses. Some or all of the viruses will then be bound to the substance according to the invention instead of the receptor on the target cells or tissues. The viruses bound to the substances according to the invention are then removed from the respiratory tract with secreted mucous material, resulting in a reduced effect of the viruses to the health of the patient. Preferably the pharmaceutical composition used is a soluble composition comprising the substances of the invention. The substance according to the invention can be attached to a carrier substance which is preferably not a protein. When using a carrier molecule, several molecules of the substance according to the invention can be attached to one carrier and the inhibitory efficiency is improved.

According to the invention it is possible to incorporate the substance according to the invention, optionally with a carrier, in a pharmaceutical composition, which is suitable for the treatment of a condition due to the presence of influenza virus in the respiratory tract of a patient or to use the substance according to the invention in a method for treatment of such conditions. Examples of conditions treatable according to the invention are virus-mediated neutrophil dysfunction which includes depression of bactericidal activity of neutrophils and stimulation apoptosis of these cells, prevention of secondary bacterial infections due the neutrophil dysfunction, and the primary infection by the influenza viruses in the respiratory tract.

The pharmaceutical composition according to the invention may also comprise other substances, such as an inert vehicle, or pharmaceutically acceptable carriers, preservatives etc. which are well known to persons skilled in the art.

The substance or pharmaceutical composition according to the invention may be administered in any suitable way, although an oral or nasal administration especially in the form of a spray or inhalation are preferred.

The term "treatment" used herein relates both to treatment in order to cure or alleviate a disease or a condition, and to treatment in order to prevent the development of a disease or a condition. The treatment may be either performed in a acute or in a chronic way.

The term "patient", as used herein, relates to any human or non-human mammal in need of treatment according to the invention.

Furthermore, it is possible to use substances specifically binding or inactivating the substances according to the invention when present on human tissues and thus to prevent the binding of influenza virus. Examples of such substances include the lectin *Sambucus nigra* agglutinin. When used in a human, such substances should be suitable for such use as a humanized antibody or an enzyme, such as recombinant sialidase of human origin which is non-immunogenic and capable of cleaving the terminal NeuNAcα6- from the substances of the invention.

It is possible to use the substance according to the invention with other pharmaceutical substance or substances effective against influenza viruses and achieve more effective pharmaceutical compositions and methods of treatment, provided that the substances used do not inactivate each other, such as the substance inactivating the substances according to the invention as described above. It is especially beneficial to use substances according to the invention together with a pharmaceutical neuraminidase (sialidase) inhibitor (Influenza virus neuraminidase inhibitors have been reviewed in The Lancet (2000), 355:827-35), which could prevent partial degradation of the substance according to the invention and prevent the viral activity with different mechanisms.

Furthermore, it is possible to use the substance according to the invention in the diagnosis of a condition caused by an influenza virus infection. Diagnostic uses also include the use of the substance according to the invention for typing of the influenza viruses. When the substance according to the invention is used for diagnosis or typing, it may e.g. be included in a probe or a test stick, optionally constituting a part of a test kit When this probe or test stick is brought into contact with a sample containing human influenza viruses, the viruses will bind the probe or test stick and can be thus removed from the sample and further analyzed.

Glycolipid and carbohydrate nomenclature is according to recommendations by the IUPAC-IUB Commission on Biochemical Nomenclature (Carbohydr. Res. 1998, 312, 167; Carbohydr. Res. 1997, 297, 1; Eur. J. Biochem. 1998, 257, 29).

It is assumed that Gal, Glc, GlcNAc, and NeuNAc are of the D-configuration, Fuc of the L-configuration, and all the monosaccharide units in the pyranose form. Glycosidic linkages are shown partly in shorter and partly in longer nomenclature, the linkages of the NeuNAc-residues α3 and α6 mean the same as α2-3 and α2-6, respectively, and β1-3, β1-4, and β1-6 can be shortened as β3, β4, and β6, respectively. Lactosamine refers to N-acetyllactosamine, Galβ1-4GlcNAc, and sialic acid is N-acetylneuraminic acid, NeuNAc. A lactose residue or a lactosamine residue can be derivatized or glycosically conjugated from position 1 of Glc/GlcNAc or correspond to a free reducing end of a non-conjugated oligosaccharide chain. In the shorthand nomenclature for fatty acids and bases, the number before the colon refers to the carbon chain length and the number after the colon gives the total number of double bonds in the hydrocarbon chain. Glc/GlcNAc indicates an oligosaccharide continuing either a Glc or a GlcNAc residue in the indicated position and 3/6, 6/3 indicates that the linkage can be either to the 3 or the 6 position.

The present invention is further illustrated in examples, which in no way are intended to limit the scope of the invention:

EXAMPLES

Abbreviations Used in the Examples

TLC, thin-layer chromatography; C, chloroform; M methanol; MAA, *Maackia amurensis* lectin; SNA, *Sambucus nigra* lectin; MALDI-TOF MS, matrix-assisted laser desorption/ionization time-of-flight mass spectrometry; FAB MS, fast atom bombardment mass spectrometry; EI MS, electron ionization mass spectrometry. We use denotations 3s to 8s to indicate migration regions on TLC plates for three- to eight-sugar-containing monosialogangliosides. S-3-PG, sialyl-3-paragloboside (NeuAcα3Galβ4GlcNAcβ-3Galβ4GlcCer); S-6-PG, sialyl-6-paragloboside (NeuAcα6Galβ4GlcNAcβ-3Galβ4GlcCer). Glycolipid and carbohydrate nomenclature, see above.

Materials and Methods

Materials. Horseradish peroxidase (HRP) labeled egg-grown influenza A viruses (human X-113 reassortant vaccine strain bearing hemagglutinin and neuraminidase of A/Texas/36/91, H1N1, and avian virus A/duck/Czechoslovakia/56, H4N6) were prepared as described before Matrosovich et al., 1996). Total ganglioside fractions were obtained from the Institute of Medical Biochemistry, Göteborg University, Sweden, and prepared according to Karlsson, 1987. Some fractions were purified by phase partition (Folch et al., 1957) before analysis, as indicated in legends to figures. The human virus-binding subfractions of human leukocyte gangliosides (FIG. 6) were prepared by preparative thin-layer chromatography (Miller-Podraza et al., 1992) followed by further purification. After separation the fractions were suspended in C/M/H2O, 60:30:4.5, by vol, applied to a small (0.25 ml) silica gel column packed in C/M, 2:1, by vol., and the sugar-positive fractions were eluted with C/M H2O, 60:35:8, by vol. Anti-sialyl-Lewis x and CDw65/clone VIM-2 monoclonal antibodies were from Seikagakut (Japan) and Dianova GmbH (Germany), respectively, and *Maackia amurensis* (MAA) and *Sambucus nigra* (SNA) letins from Boehringer-Mannheim (Germany). Silica gel aluminum plates 60 were purchased from Merck (Germany).

Preparation of leukocytes. Mixtures of human white cells were prepared from venous blood of healthy donors. The buffy coats were lysed in 0.8% $NH_4Cl$ (removal of erythrocytes, Fredlund et al., 1988) and centrifuged at 400×g. Fractions used contained from 70% to 85% of polymorphonuclear leukocytes.

Mild periodate oxidation of gangliosides (Veh et al., 1977) Gangliosides (0.05-0.1 mM) were incubated in 1-2 mM $NaIO_4$ in 0.05 mM acetate buffer, pH 5.5, for 40 min on ice, after which an excess of $Na_2SO_3$ was added. The sample was concentrated by freeze-drying (about 5-fold) and reduced with an excess of $NaBH_4$ at room temperature overnight. Finally, the sample was dialyzed against distilled water and freeze dried.

TLC-overlay binding assays. The general overlay technique was previously described (Karlsson and Strömberg, 1987). Specific applications of this technique that we utilized in this study are given below.

Overlay with influenza viruses. Plates with separated glycolipids were treated with 0.3% polyisobutylmethacrylate (Aldrich Chemical Company, Inc., Milwaukee, USA) in diethyl ether:hexane, 5:1, by vol., for 1 min, dried and incubated in 2% BSA and 0.1% Tween 20 in PBS for 2 h at room temperature. The plates were then overlaid with HRP-labeled virus suspension in 0.2% BSA, 0.01% Tween 20 in PBS and incubated as above for additional 2 h. After washing four times with PBS, the plates were visualised by incubating at room temperature (in dark) in 0.02% DAB (3,3'-diaminobenzidine tetrahydrochloride, Pierce, Rockford, Ill., USA) in PBS containing 0.03% $H_2O_2$.

Overlay with antibodies. Overlay with antibodies was performed as described earlier (Miller-Podraza et al. 1997).

Overlay with lectins on membrane blots. Detection of α3- and α6-linked sialic acids on membrane blots with lectins from *Maackia amurensis* MAA) and *Sambucus nigra* (SNA), was performed as described (Johansson et al., 1999).

Mass spectrometry. MALDI-TOF MS was performed on a TofSpec-E (Micromass, UK) mass spectrometer operated in a reflectron mode. The acceleration voltage was 20 kV and sampling frequency 500 MHz. The matrix was 6-aza-2-thiothymine dissolved in $CH_3CN$. FAB MS was performed on a SX102A mass spectrometer (JEOL) operated in a negative ion mode. The spectra were produced by Xe atoms (8 kV) using triethanolamine as matrix. EI MS of permethylated glycolipids was performed as described (Breimer et al., 1980) using the same JEOL mass spectrometer.

Example 1

Binding of Human Influenza Virus to Mixtures of Human Gangliosides

Figure 1:
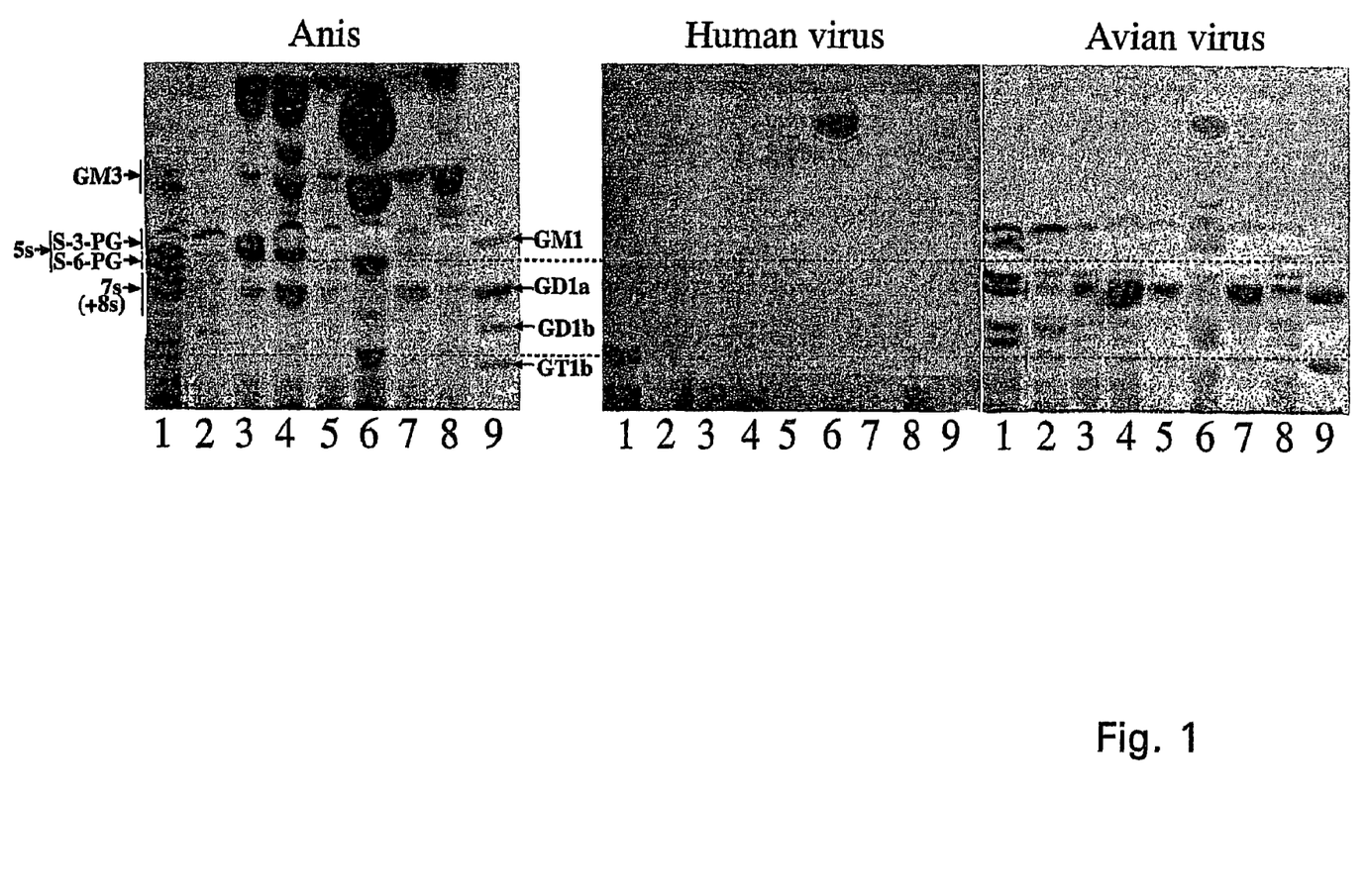
FIG. 1. Binding of HRP conjugates of human (H1N1) and avian (H4N6) influenza A viruses to gangliosides isolated from different human tissues and separated on silica gel thin-layer plates. Anis, plate sprayed with anisaldehyde (4-methoxybenzaldehyde); Human virus and Avian virus, plates overlayed with respective conjugates. Lane 1, upper phase gangliosides (after Folch's partition) from human leukocytes; Lane 2, upper phase gangliosides from human erythrocytes; Lane 3, total gangliosides from human small intestine, sample 1; Lane 4, total gangliosides from human small intestine, sample 2; Lane 5, total gangliosides from human stomach; Lane 6, total gangliosides from human meconium; Lane 7, total gangliosides from human colon; Lane 3, total gangliosides from human pancreas; Lane 9, bovine brain gangliosides. The plates were developed in Chloroform/Methanol/0.25% KCl in $H_2O$, 50:40:10. S-3-PG, sialyl-3-paragloboside; S-6-PG, sialyl-6-paragloboside; 5s, 7s and 8s, 5-, 7- and 8-sugar-containing monosialoganglioside fractions ($NeuAc_1Hex_3HexNAc_1Cer$, $NeuAc_1Hex_4HexNAc_2Cer$ and $Fuc_1NeuAc_1Hex_4HexNAc_2Cer$, respectively). To visualize slowly migrating gangliosides some lanes were overloaded. Dotted lines were drawn to facilitate interpretation.

FIG. 1 shows binding of human and avian influenza viruses (avian viruses were used as a control experiment) to reference gangliosides (lane 9) and to mixtures of gangliosides isolated from different human tissues (lanes 1-8). The human influenza virus did not bind in the assay conditions to shorter gangliosides including abundant 5s and 7s species, but displayed a strong and selective binding to some extended glycolipids of human leukocytes (lane 1 in FIG. 1). There was also a weak binding to slow-moving species of other human tissues, in particular small intestine and pancreas (lanes 4 and 8). The avian virus bound to a variety of gangliosides in all lanes including two fractions of reference brain gangliosides, and displayed a preference for NeuAcα3Gal-terminated species as compared with NeuAcα6Gal-terminated species and species with sialic acid as internal branches. As shown in the figure, there was a binding to NeuAcα3-paragloboside (S-3-PG) and gangliosides GD1a and GT1b (see Table 1 for structures), but not to NeuAcα6-paragloboside (S-6-PG) or gangliosides GM1 or GD1b. These results agree with earlier reports on avian influenza virus binding specificities (see refs. in Introduction). The binding to GM3 was however not observed, although some lanes were overloaded with respect to less complex components. Binding to the fastest-moving band by both viruses in lane 6 of FIG. 1 was probably unspecific interaction with overloaded and charged sulfatide.

Example 2

Mild Periodate Oxidation of the Gangliosides

Figure 2:
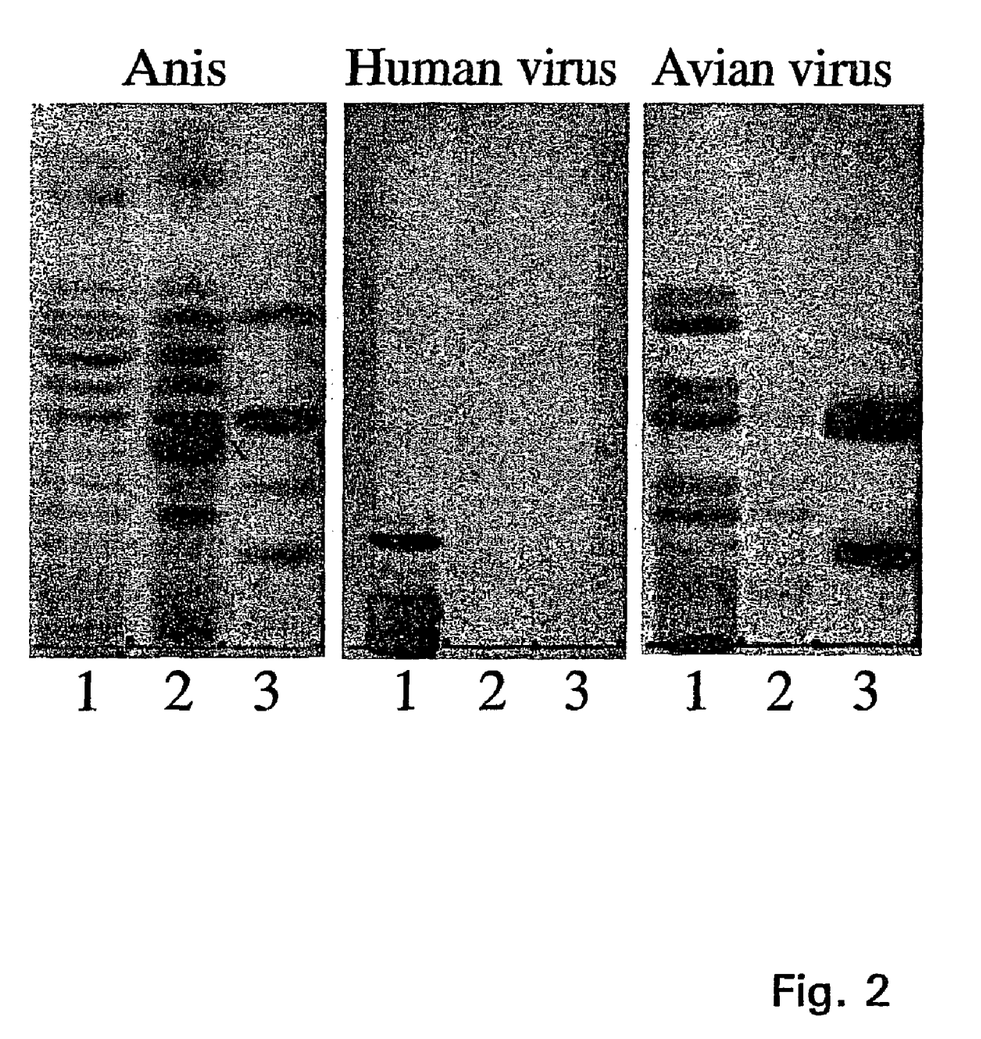
FIG. 2. Binding of human and avian influenza viruses HRP conjugates to leukocyte gangliosides on silica gel TLC plates before (lane 1) and after (lane 2) mild oxidation and reduction. Lane 3: reference brain gangliosides (from top: GM1, GD1a, GD1b, GT1b). Anis, gangliosides stained with anisaldehyde. Chromatographic conditions were as in FIG. 1. x, non-sugar spot acquired during dialysis.
Figure 3A:
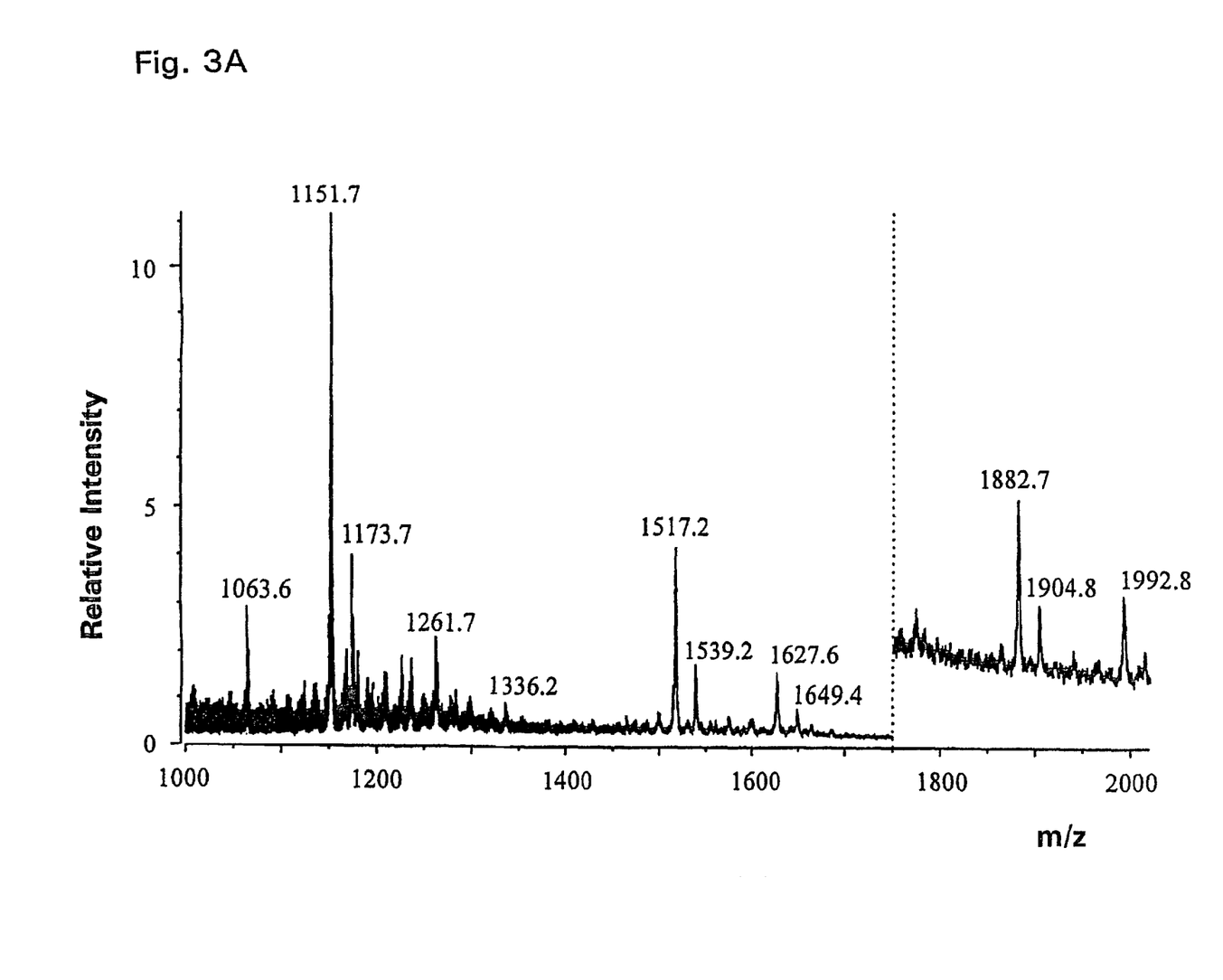
FIG. 3A. Negative ion FAB mass spectra of gangliosides from human leukocytes before mild periodate oxidation and reduction.
Figure 3B:
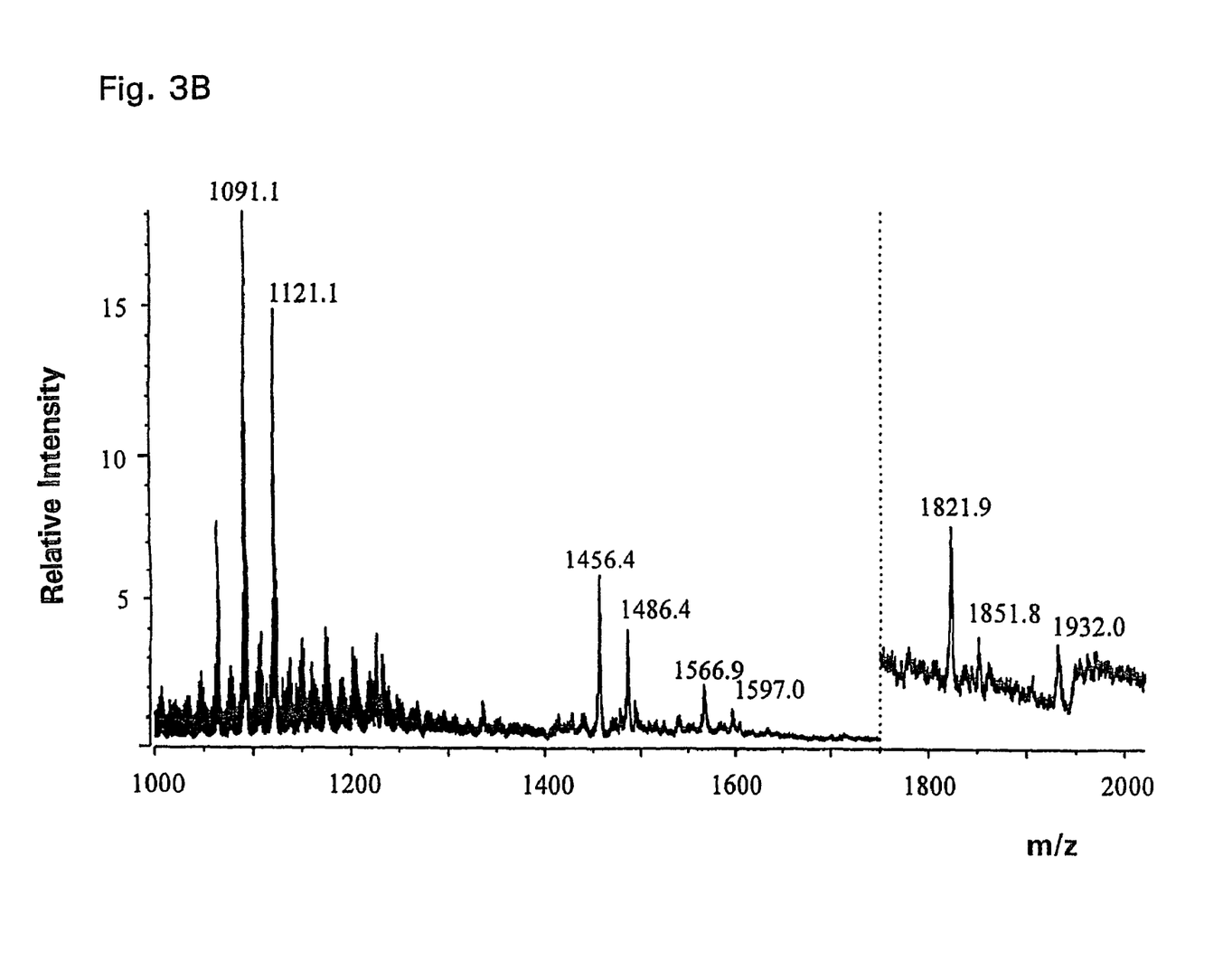
FIG. 3B. Negative ion FAB mass spectra of gangliosides from human leukocytes after mild periodate oxidation and reduction.
Figure 4A:
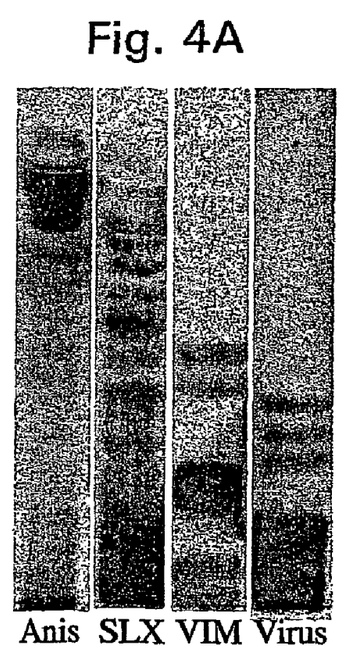
FIG. 4A. Binding of anti-sialyl-Lewis x (SLX) and Vim-2 (VIM) monoclonal antibodies to upper phase gangliosides (after Folch's partition) of human leukocytes separated on silica gel TLC plates. Anis, gangliosides stained with anisaldehyde; Virus, gangliosides overlaid with human influenza virus BRP conjugate. The plates were developed in Chloroform/Methanol/0.25% KCl, 50:55:13.
Figure 4B:
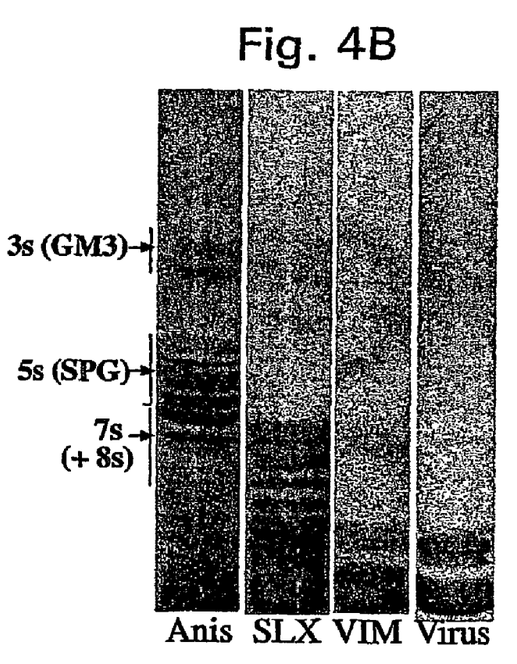
FIG. 4B. Binding of anti-sialyl-Lewis x (SLX) and Vim-2 (VIM) monoclonal antibodies to upper phase gangliosides (after Folch's partition) of human leukocytes separated on silica gel TLC plates. Anis, gangliosides stained with anisaldehyde; Virus, gangliosides overlaid with human influenza virus HRP conjugate. The plates were developed in Chloroform/Methanol/0.25% KCl, 50:40:10.
Figure 5:
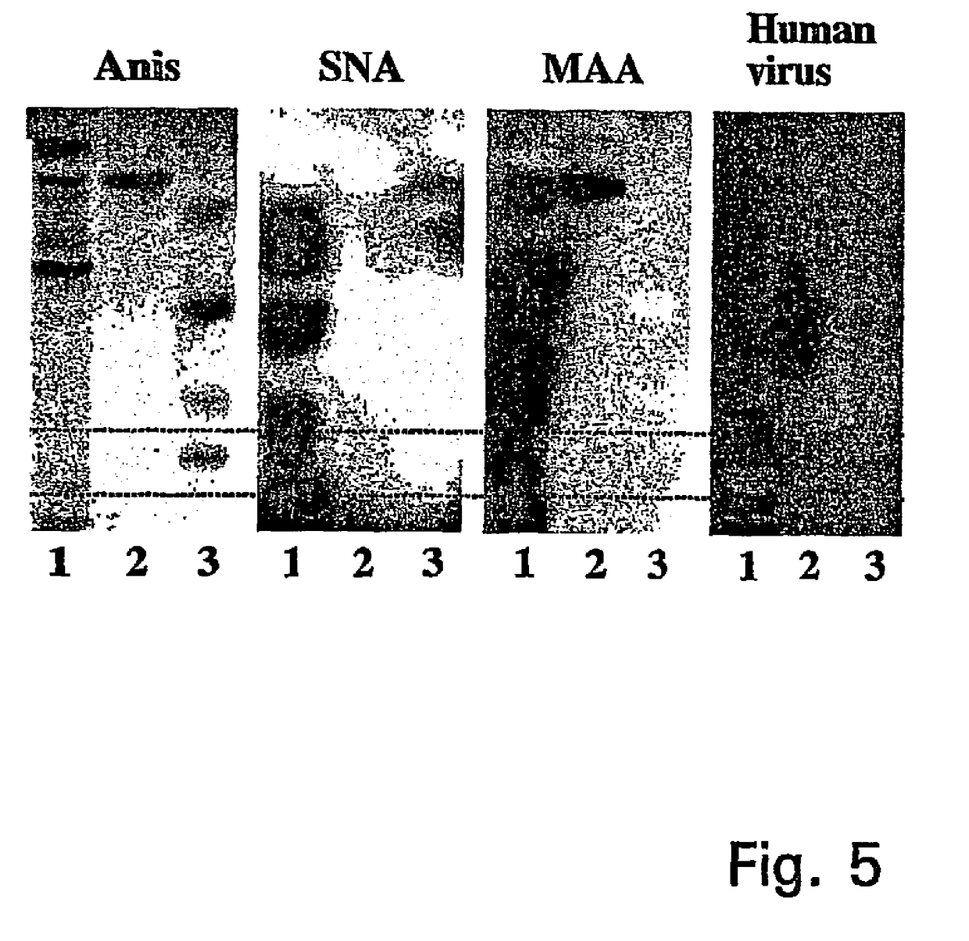
FIG. 5. Binding of NeuAcα3- and NeuAcα6-specific lectins from *Maackia amurensis* (MAA) and *Sambucus nigra* (SNA) to gangliosides separated by TLC and blotted to PVDF membranes; Human virus, binding of human virus HRP conjugate on the corresponding TLC plate; Anis, TLC plate with separated gangliosides and visualized with anisaldehyde. The plates were developed in Chloroform/Methanol/0.250% KCl, 50:50:13. Lane 1, upper phase gangliosides (after Folch's partition) from human leukocytes; Lane 2, sialyl-3-paragloboside; Lane 3, bovine brain gangliosides (GM1, GD1a, GD1b and GT1b).

To exclude binding to sulfated glycolipids in other lanes we used mild periodate oxidation and reduction which shortens specifically the sialic acid glycerol tail in gangliosides by one or two carbon atoms (Veh et al., 1977). Binding of influenza viruses to sulfated galactosylceramide was previously reported by Suzuki et al., 1996. The mild oxidation eliminated in our studies completely (human influenza) or almost completely (avian virus) binding to leukocyte glycolipids, as shown in FIG. 2. The result confirms the specific importance of the sialic acid for the virus attachment, and agrees with previous studies on binding of influenza viruses to chemically modified carbohydrates (Suttajit and Winzler, 1971; Matrosovich et al., 1991).

The oxidized and reduced gangliosides were tested by FAB MS and by EI MS after permethylation. In FAB MS spectra the pseudomolecular ions $[M-H]^-$ seen clearly for 3s, 5s and 7s gangliosides were reduced by 30 or 60 (±1) mass units, see FIG. 3. Thus, the main ions in FIG. 3A at m/z 1151.7(GM3, d18:1-16:0), 1517.2 (SPG, d18:1-16:0) and 1882.7 (7s, d18: 1-16:0) were replaced after oxidation and reduction in FIG. 3B by ions at 1091.1 and 1121.1, 1456.4 and 1486.4, and 1821.9 and 1851.8, respectively. In EI MS spectra the NeuAc fragment ions at m/z 376 and 344, were replaced after oxidation and reduction by m/z at 332 and 300, and 288 and 256 (not shown). Degradation of the core chains was not observed.

Example 3

Analysis of the Human Influenza Receptor Glycolipids by Antibodies

To test if the binding of the human virus was to the monofucosylated sialyl-Lewis x or VIM-2-active saccharides as reported earlier (Suzuki, 1994; Müthing, 1996), we used overlay of TLC plates with antibodies which react with these structures (FIG. 4). The polar solvent (A) allowed clear separation of VIM-2- and virus-positive fractions (FIG. 4A, lanes VIM and Virus), at least within the less complex region. There was an overlapping of anti-sialyl-Lewis x and human virus bindings (FIGS. 4A and 4B, lanes SLX and Virus), but the patterns were not identical, and there was no recognition by the virus of less complex sialyl-Lewis x-positive molecules.

Example 4

Characterization of the Human Influenza Receptor Glycolipids by Lectins

FIG. 5 shows binding of MAA and SNA (lectins specific for α3- and α6-linked NeuAc, respectively) to leukocyte gangliosides in comparison with binding by human influenza virus. There was a co-migration of the more complex virus- and SNA-positive fractions, however, there was no binding of the virus to the less complex SNA-positive bands. The latter were earlier identified as 5s and 7s gangliosides with 6-linked NeuAc (Johansson and Miller-Podraza, 1998). MAA, which binds specifically to NeuAcα3-containing carbohydrate chains of the neolacto series (Knibbs et al., 1991; Johansson et al., 1999), displayed a completely different pattern of binding than the virus. Binding of the human virus to minor NeuAcα6-containing species were reproduced after ganglioside separation in a second TLC solvent (not shown). The weak binding of the virus seen in lane 3 of FIG. 5 could represent cross reaction with brain gangliosides. However this binding was not reproducible (see FIG. 1).

In an attempt to identify sequences that display efficient binding of human virus, gangliosides from human leukocytes were separated by preparative TLC and tested again for the binding (FIG. 6). The most complex fractions were not analysed in this way because of inadequate amounts and poor separation. Two fractions were shown to contain active components, see Fr. 5 and Fr. 6 in the figure. Tests in different chromatographic systems (TLSC not shown) revealed however that the main components in these subfractions were inactive and that binding was to some minor overlapping fractions. This agrees with the fact that the binding was to slowly migrating NeuAcα6-containing species (FIG. 5), which have earlier been detected by SNA lectin (Johansson and Miller-Podraza, 1998). They occur in human leukocytes in very small amounts and so far only NeuAcα3-containing structures were detected by chemical methods among more complex gangliosides isolated from this source (Müthing et al., 1996; Stroud et al., 1995; Stroud et al., 1996). The detection level on TLC plates by the human virus was 40-80 pmol in relation to the total ganglioside mixture, and apparently much lower for the active species, indicating that the binding was highly efficient (see binding to trace fractions in lane 6 of FIG. 6)

Example 5

Mass Spectrometry of Glycolipid Fractions Containing Receptors for Human Influenza Viruses The most active isolated fraction (Fr. 6 of FIG. 6) was shown by MALDI-TOF mass spectrometry to contain complex gangliosides with 8-11 monosaccharides per mol of ceramide (FIG. 7 and Table 2). Fragmentation pattern seen in FAB MS analysis confirmed the presence of oligosaccharide chains with repeated HexHexNAc units (spectra not shown). The most abundant molecular ions corresponded to $NeuAc_1Fuc_1Hex_5HexNAc_3Cer$ at m/z 2394.0 and $NeuAc_1Hex_5HexNAc_3Cer$ at 2248.7. As mentioned, the main components were excluded as binding molecules by TLC in different solvent systems. The most probable candidates of the active species were therefore minor disialylated or difucosylated gangliosides with 2 or 3 lactosamine units. Monofucosylated gangliosides $NeuAc_1Fuc_1Hex_4HexNAc_2Cer$, (8s), (m/z at 2030.4 in FIG. 7) with two N-acetyllactosamine units are less likely as binding molecules, as judged from chromatographic mobility and binding tests, see FIGS. 1, 4B and 6, (8s region). In Fr. 5 of FIG. 6 the main (non-active) component was $NeuAc_1Hex_5HexNAc_3Cer$.

Example 6

Analysis of Data from Mass Spectrometry and TLC-Experiments

The direct characterization of the exact binding structures was not possible because of the low amount of the material and presence of several active species. However, we have excluded sialyl-Lewis x and VIM-2-active saccharides (Table 1, FIG. 4) as the binding sequences. We have also shown using SNA lectin that the binding was to some minor NeuAcα6-containing species (FIG. 5). In addition, we have demonstrated, that the binding was dependent on the presence of the unchanged glycerol sialic acid tail (FIGS. 2 and 3). Our results therefore do not support earlier suggestions on a preferential binding of human influenza A viruses to sialyl-Lewis x (Suzuki, 1994) or VIM-2-active structures (Suzuki, 1994; Müthing, 1996). This discrepancy may be caused by differences in virus stains. The cited authors used influenza viruses A/PR/8/34 (H1N1) and the reassortant virus strain X-31, which bear HA and NA genes of A/Aichi/2/28 (H3N2), while we studied human influenza virus X-113 (HA and NA genes of A/Texas/36/91, H1N1). PR/8/34 and X-31 are known to have a higher affinity to NeuAcα3-containing receptors than more recently circulated influenza A viruses (Rogers and D'Souza, 1989; Matrosovich et al., 1997), and this may explain strong interaction of PR/8/34 and X-31 with sialyl-Lewis x and VIM-2 structures and no binding to these structures in our tests. There was an overlapping binding by anti-sialyl-Lewis x antibody and the human virus in our studies (FIG. 4). However, the overall patterns were not identical and there was no interaction of the virus with less complex sialyl-Lewis x gangliosides reported to be present in human leukocytes (Müthing et al., 1996). We have detected by FAB MS in fractions 1 through 3 (FIG. 6) increasing amounts of 8s gangliosides with a potential sialyl-Lewis x composition of $Fuc_1NeuAc_1Hex_4HexNAc_2Cer$ with various ceramides (m/z at 2028.7 and 2138.4, not shown). These gangliosides migrated in the 7s region overlapping with more abundant non-fucosylated $NeuAc_1Hex_4HexNAc_1Cer$ fractions. Of importance is a binding in this region of anti-sialyl-Lewis x antibody, but not of either VIM-2 antibody or virus (FIG. 4). Structural microheterogeneity associated with ceramide parts and NeuAcα3/α6 substitutions may explain the overlapping migration of different gangliosides and the complex multi-band patterns in lanes SLX of FIG. 4. The cross-binding to other fucosylated structures (Stroud et al., 1995) of the lower TLC regions, may also contribute to these complex patterns.

Figure 6:
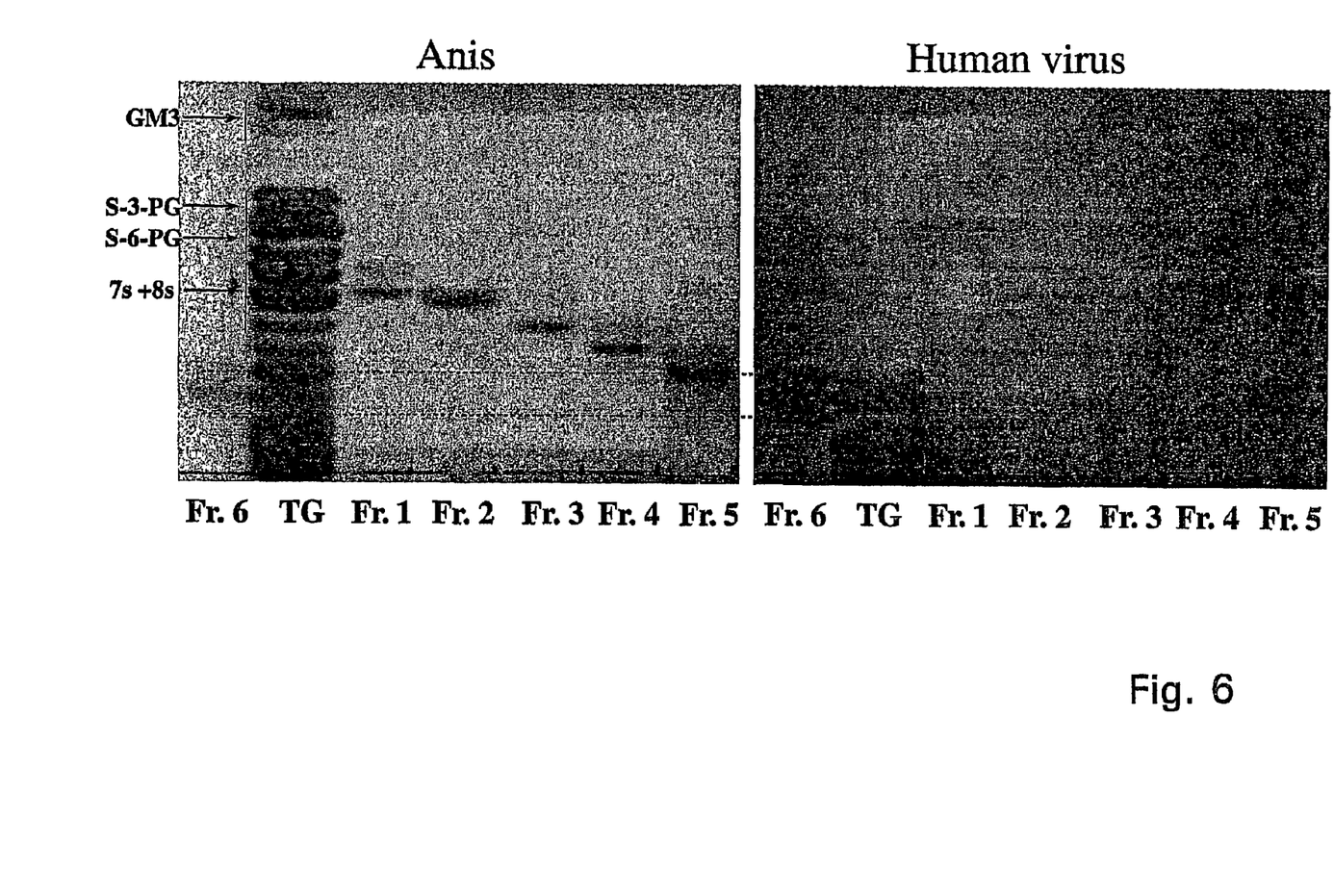
FIG. 6. Binding of HRP conjugate of human (A, H1N1) influenza virus to ganglioside subflactions (Fr. 1-6) obtained from a mixture of human leukocyte gangliosides after preparative TLC; TG, Total ganglioside mixture. Anis, plate visualized with anisaldehyde; Human virus, plate overlaid with virus conjugate.

We have excluded that the main components of fractions 5 and 6 in FIG. 6 are binding molecules by TLC analysis in different solvent systems and overlay tests. Table 2 lists (in bold) candidates of active species which we could detect by MALDI-TOF MS. Of importance for the binding could be oligosialylation and/or repeated fucose branches, as judged from the presence of disialylated molecules and/or difucosylated molecules in the mixture (difference between masses of 2Fuc and 1NeuAc is only 1.03 amu). Like the oligosialylated species the monosialylated glycolipid may also be branched by β6-linked lactosamine unit, molecular mass of such minor species would overlap the major non-active glycolipid with [M-H]$^-$ molecular mass at 2248.5. Also length of the sugar should be considered as an important factor, since only complex gangliosides were binding. The extended carbohydrate chains may serve as spacers which reduce steric hindrance to recognition by viral hemagglutinins. It has been shown, that glycosylation of viral HAs in the vicinity of the receptor binding sites may decrease the virus binding to target cells and immobilized receptors (Matrosovich et al., 1997; Gambaryan et al., 1998; Ohuchi et al., 1997). The impaired accessibility of the receptor binding pocket could explain why we did not see binding of the human influenza to less complex gangliosides like GM3 or SPG. In fact, the hemagglutinin of X-113 reassortant human virus, although not yet sequenced, is likely to contain glycans at $Asn_{129}$ and $Asn_{163}$ close to the tip of the HA globular head, similar to the HAs of other contemporary H1N1 human viruses, for which sequences are available. In contrast, the avian virus strain A/duck/Czechoslovakia/56 (H4N6) lacks carbohydrates in this portion of the HA (Matrosovich et al., 1999). Also Müthing (Müthing, 1996) emphasized a stronger binding to longer fucosylated species (sialyl-Lewis x- and VIM-2-active species) compared to 5s and 7s gangliosides using X-31 (H3N2) influenza A strain.

In our studies there was however no binding at all to 5s NeuAcα6-containing SPG nor to its 7s homologue, although the interaction of the human virus with some selected complex species was very strong (for characterization of 5s and 7s gangliosides of human leukocytes see Johansson and Miller-Podraza, 1998). Technical assay reasons for this unusual binding are unlikely, since the avian virus bound to S-3-PG and to other well defined common gangliosides under the same experimental conditions (FIG. 1). It is reasonable to assume, that both length and structural features of the receptor chain contributed to this result. Gangliosides with branched N-acetyl-lactosamine chains and NeuAc on more than one arm should be considered as highly efficient binding molecules. Polyvalency has earlier been shown as an important factor enhancing binding affinity of influenza virus to synthetic sialylated compounds (Mammen et al., 1995), and branched polyglycosylceramides were very effective receptors for human influenza A and B viruses (Matrosovich et al., 1996). The calculated molecular masses of the disialylated species having similar ceramide structures as previous reported from the human leukocyte gangliosides (Stroud et al., 1996b; Müthing, 1996) matched closely to the experimental data in Table 2. Branched α3 monosialylated polylactosamine ganglioside has been described from human gangliosides (Stroud et al, 1996b). Human leukocytes are known to contain neolacto glycolipids with repeated fucose residues as Fucα3GlcNAc units (Stroud et al., 1995; Stroud et al., 1996; Müthing, 1996), corresponding molecular weights are also seen in our analyses, see Table 2. Fucose may possibly interact with the hydrophobic methyl group with spots outside the NeuAc binding site of the viral HA. In fact, synthetic NeuAc analogues with hydrophobic neighbouring groups have been shown to interact with hydrophobic patches adjoining the receptor binding site of influenza virus A hemagglutinin, considerably improving affinity (Watowich et al., 1994).

TABLE 1

Carbohydrate and glycolipid structures discussed in this paper

NeuAcα3Galβ4GlcβCer
GM3, 3s ganglioside
Galβ3GalNAcβ4(NeuAcα3)Galβ4GlcβCer
GM1
NeuAcα3Galβ3GalNAcβ4(NeuAcα3)Galβ4GlcβCer
GD1a
Galβ3GalNAcβ4(NeuAcα8NeuAcα3)Galβ4GlcβCer
GD1b
NeuAcα3Galβ3GalNAcβ4(NeuAcα8NeuAcα3)Galβ4GlcβCer
GT1b
NeuAcα3Galβ4GlcNAcβ3Galβ4GlcβCer
S-3-PG, NeuAc-3-paragloboside, sialyl-3-paragloboside, 5s ganglioside
NeuAcα6Galβ4GlcNAcβ3Galβ4GlcβCer
S-6-PG, NeuAc-6-paraglobiside, sialyl-6-paragloboside, 5s ganglioside
NeuAcα3Galβ4GlcNAcβ3Galβ4GlcNAcβ3Galβ4GlcβCer
7-sugar NeuAc-3-neolacto ganglioside, 7s ganglioside
NeuAcα6Galβ4GlcNAcβ3Galβ4GlcNAcβ3Galβ4GlcβCer
7-sugar NeuAc-6-neolacto ganglioside, 7s ganglioside
NeuAcα3Galβ4(Fucα3)GlcNAcβ-
Sialyl-Lewis x epitope
NeuAcα3Galβ4GlcNAcβ3Galβ4(Fucα3)GlcNAcβ-
"VIM-2" epitope (epitope reacting with CDw65/clone VIM-2 monoclonal antibody)

TABLE 2

Figure 7:
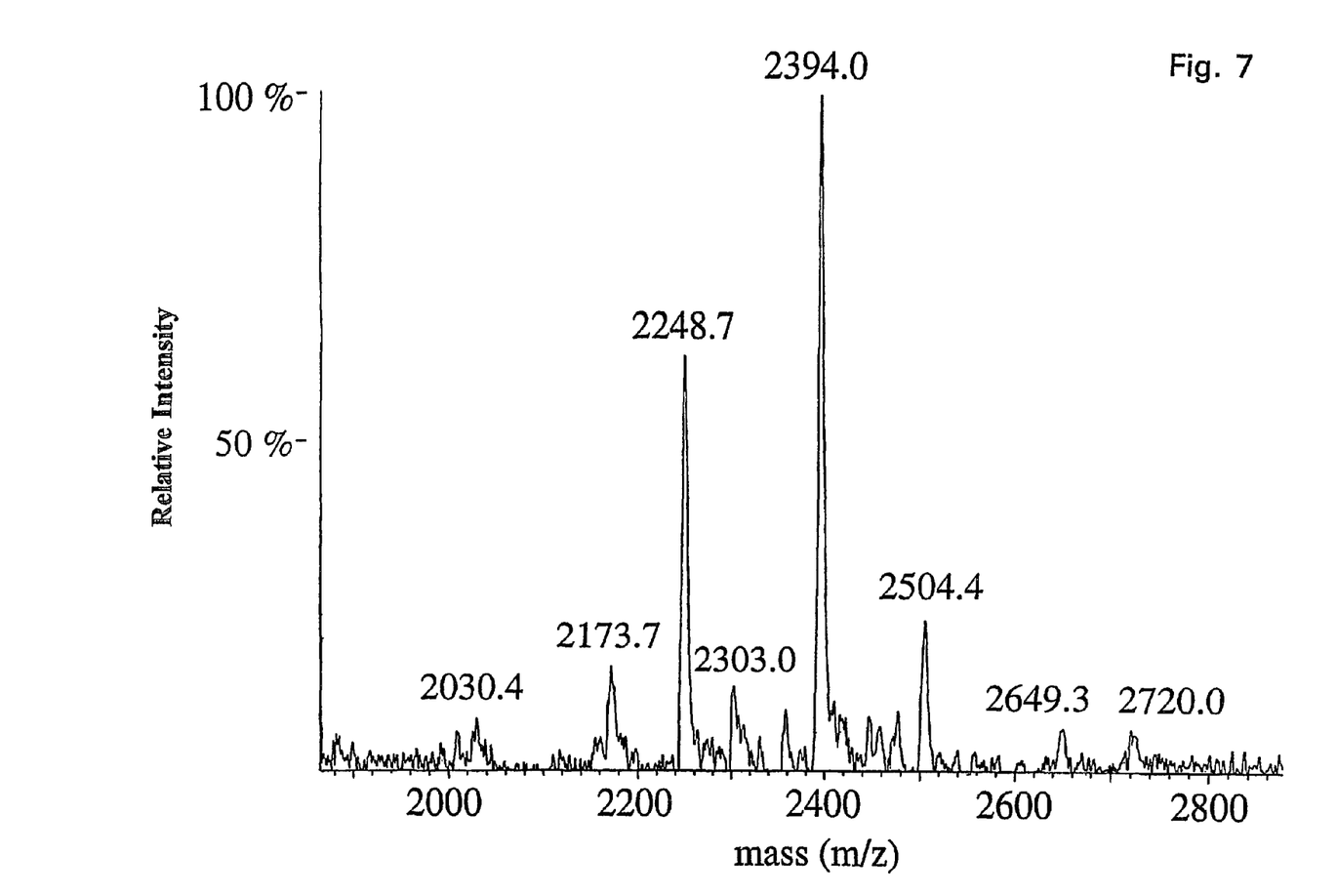
FIG. 7. MALDI TOF spectrum of ganglioside fraction 6 of FIG. 6. Mass spectrometer was operated in a negative-ion reflectron mode.

Ganglioside composition of fraction 6 (Fr. 6 in FIG. 6) based on MALDI-TOF-MS mass spectrometry. The spectrum is shown in FIG. 7. The most probable binding components (as judged from combined results) are in bold.

| M-H Observed | M-H Calculated | ΔM | Most probable compositions (listed according to decreasing abundance) |
|---|---|---|---|
| 2394.0 | 2394.6 | −0.6 | NeuAc$_1$Fuc$_1$Hex$_5$HexNAc$_3$Cer (d18:1-16:0) |
| 2248.7 | 2248.5 | +0.2 | NeuAc$_1$Hex$_5$HexNAc$_3$Cer (d18:1-16:0) |
| 2504.4 | 2504.8 | −0.4 | NeuAc$_1$Fuc$_1$Hex$_5$HexNAc$_3$Cer (d18:1-24:1) |
| 2173.7 | 2174.4 | −0.7 | NeuAc$_2$Hex$_4$HexNAc$_2$Cer (d18:1, 16:0) and/or |
|  | 2173.4 | +0.3 | NeuAc$_1$Fuc$_1$Hex$_4$HexNAc$_2$Cer (d18:1-16:1) |
| 2649.3 | 2649.9 | −0.6 | NeuAc$_2$Hex$_5$HexNAc$_3$Cer (d18:1-24:1) and/or |
|  | 2651.0 | −1.7 | NeuAc$_1$Fuc$_2$Hex$_5$HexNAc$_3$Cer (d18:1-24:1) and/or |
|  | 2649.0 | +0.3 | NeuAc$_1$Fuc$_2$Hex$_5$HexNAc3Cer (d18:1-24:2) |
| 2030.4 | 2029.3 | +1.1 | NeuAc$_1$Fuc$_1$Hex$_4$HexNAc$_2$Cer (d18:1-16:0) |

REFERENCES

Abramson, J. S. and Hudnor, H. R. (1995) *Blood*, 85, 1615-1619.

Abramson, J. S. and Mills E. L. (1988) *Rev. Infect. Dis.*, 10, 326-341.

Baum, L. G., and Paulson, J. C. (1990) *Acta Histochem.*, Suppl. XL, 35-38;

Breimer, M., Hansson, G. C., Karlsson, K.-A., Larsson, G., Leffler, H., Pascher, I., Pimlot W. and Samuelsson, B. E. (1980) In: *Advances in Mass Spectrometry, Vol. 8* (A. Quayle, ed.) pp. 1097-1108., London: Heyden & Son.

Cassidy, L. F., Lyles, D. S. and Abramson, J. S. (1989) *J. Immunol.*, 142, 4401-4406.

Clarke, J. L., and Watkins, W. M. (1996) *J. Biol. Chem.*, 271, 10317-10326

Colamussi, M. L., White, M. R, Crouch, E., Hartshorn, K. L. (1999) *Blood*, 93, 2395-2403.

Connor, R. J., Kawaoka, Y., Webster, R. G. and Paulson, J. C. (1994) *Virology*, 205, 17-23.

Daigneault, D. E., Hartshorn, K. L., Liou L. S., Abruzzi, G. M., White M. R., Oh, S.-K. and Tauber, A. I. (1992) *Blood*, 80, 3227-3234.

de Vries, T., Srnka, C. A. Palcic, M. P., Swiedler, S. J., van den Eijnden, D. H., and Macher, B. A. (1995) *J. Biol. Chem.*, 270, 8712-8722

Eisen, M. B., Sabesan, S., Skehel, J. J. and Wiley D. C. (1997) *Virology*, 232, 19-31.

Folch, J., Lees M. and Sloane-Stanley, G. H. (1957) *J. Biol. Chem.*, 226, 497-509.

Fredlund, H., Olcén, P. and Danielsson, D. (1988) *APMIS*, 96, 941-949.

Gambaryan, A. S., Piskarev, V. E., Yamskov, I. A., Sakharov, A. M., Tuzikov, A. B., Bovin, N. V., Nifant'ev, N. E. and Matrosovich, M. N. (1995) *FEBS Lett.*, 366, 57-60.

Gambaryan, A. S., Tuzikov, A. B., Piskarev, V. E., Yamnikova, S. S.; Lvov D. K, Robertson, J. S., Bovin, N. V. and Matrosovich, M. N. (1997) *Virology*, 232, 345-350.

Gambaryan, A. S., Marinina, V. P., Tuzikov, A. B., Bovin, N. V., Rudneva, I. A., Sinitsyn, B. V., Shilov, A. A., and Matrosovich, M. N. (1998) *Virology*, 247, 170-177.

Herrler, G., Hausmann, J. and Klenk, H.-D. (1995) In: *Biology of the sialic acids*, Abraham Rosenberg, ed. Plenum Press, New York pp. 315-335.

Johansson, L. and Miller-Podraza, H. (1998) *Anal. Biochem.*, 265, 260-268.

Johansson, L., Johansson, P. and Miller-Podraza, H. (1999) *Analytical Biochemistry*, 267, 239-241.

Karlsson, K.-A. (1987) *Methods Enzymol.*, 138, 212-220.

Karlsson, K.-A. and Strömberg, N. (1987) *Methods Enzymol.*, 138, 220-232.

Knibbs, R. N., Goldstein, I. J., Ratcliffe, R. M. and Shibuya, N. (1991) *J. Biol. Chem.*, 266, 83-88.

Larsen, R. D., Rivera-Marrero, C. A., Ernst, L. K., Cumming, R. D. and Lowe, J. B. (1990) *J. Biol. Chem.* 265, 7055-7061

Laver, W. G., Bischofberger, N. and Webster, R. G. (1999) *Sci Amer.*, 280, 56-65.

Mammen, M., Dahmann, G. and Whitesides, G. M. (1995) *J. Med. Chem.*, 38, 4179-4190.

Matrosovich, M. N. (1989) *FEBS Letters*, 252, 11-4.

Matrosovich, M. N., Gbaryan, A. S., Reizin, F. N., and Chumakov M. P. (1991) *Virology*, 182, 879-882.

Matrosovich, M., Miller-Podraza, H., Teneberg, S., Robertson, J. and Karlsson, K.-A. (1996) *Virology*, 223, 413-416.

Matrosovich, M. N. Gambayan, A. S., Teneberg, S., Piskarev, V. E., Yamnikova, S. S., Lvov, D. K, Robertson, J. S. and Karlsson, K.-A. (1997) *Virology*, 233, 224-234.

Matrosovich, M., Zhou, N., Kawaoka, Y., and Webster, R. (1999) *J. Virol*, 73, 1146-1155.

Mattila, P., Salminen, H., Hirvas, L., Niittymäki, J., Salo, H., Niemela, R., Fukuda, M., Renkonen, O., and Renkonen, R. (1998) *J. Biol. Chem.*, 272, 27633-27639

Miller-Podraza, H., Månsson, J.-E. and Svennerholm, L. (1992) *Biochim. Biophys. Acta*, 1124, 45-51.

Miller-Podraza, H., Stenhagen, G., Larsson, T., Andersson, C. and Karlsson, K.-A. (1997) *Glycoconjugate J.*, 14, 231-239.

Müthing, J., Unland, F., Heitmann, D., Orlich, M., Hanisch, F.-G., Peter-Katlinic, J., Knäuper, V., Tschesche, H., Kelm, S., Schauer, R. and Lechmann, J. (1993) *Glycoconjugate J.*, 10, 120-126.

Müthing, J. (1996) *Carbohydrate Res.*, 290, 217-224.

Müthing, J., Spanbroek, R, Peter-Katalinc, J., Hanisch, F.-G., Hanski, C., Hasegawa, A., Unland, F., Lehmann, J., Tschesche, and Egge, H. (1996) *Glycobiology*, 6, 147-156.

Niemelä, R., Natunen J., Majuri, M. L., Maaheimo, H., Helin, J., Lowe, J. B., Renkonen, O., and Renkonen, R. (1998) *J. Biol. Chem.*, 273, 4021-4026

Ohuchi, M., Ohuchi, R., Feldmann, A., and Klenk, H. D. (1997) *J. Virol.*, 71, 8377-8384.

Paulson J. C. (1985) In *"The Receptors"*, (M. Corn, Ed.), Vol. 2, pp-131-219, Academic Press, Orlando.

Paulson, J. C., Prieels, J. P., Glasgow, L. R, Hill, R. L. (1978) *J. Biol. Chem.*, 253, 5617-5624

Pritchett, T. J. and Paulson, J. C. (1989) *J. Biol. Chem.*, 264, 9850-9858.

Rogers, G. N. and Paulson, J. C. (1983) *Virology*, 127, 361-373.

Rogers, G. N. and D'Souza, B. L. (1989) *Virology*, 173, 317-322.

Sabesan, S., Duus, J.Ø., Neira, S., Domaille, P., Kelm, S., Paulson, J. C. and Bock, K. (1992), *J. Am. Chem. Soc.*, 114, 8363-8375

Stroud, M. R, Handa, K., Ito, K., Salyan, M. E. K., Fang, H., Levery, S. B., Hakomori, S.-i., Reinhold, B. B. and Reinhold, V. N. (1995) *Biochim. Biophys. Res. Commun.*, 209, 777-787.

Stroud, M. R, Handa, K., Salyan, M. E. K, Ito, K., Levery, S. B. and Hakomori, S.-i. (1996) *Biochemistry*, 35, 770-778.

Stroud, M. R., Handa, K., Salyan, M. E. K., Ito, K, Levery, S. B. and Hakomori, S.-i. (1996b) *Biochemistry*, 35, 758-769

Suttajit, M. and Winzler, R. J. (1971) *J. Biol. Chem.*, 246, 3398-3404.

Suzuki, Y., Nagao, Y., Kato H., Suzuki, T. and Matsumoto, M. (1985) *J. Biochem.*, 98, 1653-1659

Suzuki, Y., Nagao, Y., Kato, H., Matsumoto M., Nerome, K., Nakajima, K. and Nobusawa E. (1986) *J. Biol. Chem.*, 261, 17057-17061

Suzuki, Y., Nagao, Y., Kato, H., Suzuki, T., Matsumoto, M. and Murayma, J.-i. (1987) *Biochim. Biophys. Acta*, 903, 417-424.

Suzuki, Y., Nakao, T., Ito, T., Watanabe N., Toda, Y., Xu, G., Suzuki, T., Kobayashi, T., Kimura, Y., Yamada, A., Sugawara, K., Nishimura, H., Kitame, F., Nakamura, K., Deya, E., Kiso, M. and Hasegawa, A. (1992) *Virology*, 189, 121-131.

Suzuki, Y. (1994) *Prog. Lipid Res.*, 33, 429-457.

Suzuki, T., Sometani, A., Yamazaki, Y., Horiike, G., Mizutani, Y., Masuda, H., Yamada, M., Tahara, H., Xu, G., Miyamoto, D., Oku, N., Okada, S., Kiso, M., Hasegawa, Ito, T., Kawaoka, Y. And Suzuki, Y. (1996) *Biochem. J.*, 318, 389-393.

Watowich, S. J., Skehel, J. J. and Wiley, D. C. (1994) *Structure*, 2, 719-731.

Veh, R. W., Corfield, A. P., Sander M. and Schauer, R. (1977) *Biochim. Biophys. Acta*, 486, 145-160.

Wiley, D. C. and Skehel, J. J. (1987) *Annu. Rev. Biochem.*, 56, 365-394.

The invention claimed is:

1. A method for the treatment of a condition caused by human influenza virus, said method comprising administering a pharmaceutically effective amount of a substance to a patient in need thereof, wherein said substance comprises at least one oligosaccharide chain, said oligosaccharide chain comprising a terminal NeuNAcα6 linked to
   (a) a branched polylactosamine type structure consisting of at least three lactosamine residues glycosidically linked to each other, wherein:
   the structure optionally contains one or more additional NeuNAcα6 residues at a terminal position in a branch; and/or
   (b) a branched structure consisting of two lactosamine and one lactose residue glycosidically linked to each other, wherein:
   the structure optionally contains one or more additional NeuNAcα6 residues at a terminal position of the branch, and wherein said substance contains two NeuNAcα6 residues in a branched structure.

2. A method for the treatment of a condition caused by human influenza virus, said method comprising administering a pharmaceutically effective amount of a substance to a patient in need thereof, wherein said substance comprises at least one oligosaccharide chain, said oligosaccharide chain comprising a terminal NeuNAcα6 linked to
   (a) a linear polylactosamine type structure consisting of at least three lactosamine residues glycosidically linked to each other, wherein:
   the structure contains optionally one or two fucose residues, each of which is α3-linked to a GlcNAc-residue of a lactosamine residue to which the terminal NeuNAc is not α6-linked; and/or
   (b) a linear or branched structure consisting of two lactosamine and one lactose residue glycosidically linked to each other, wherein:
   the structure additionally contains one or two fucose residues, each of which is α3-linked to GlcNAc-residue of a lactosamine residue to which the terminal NeuNAc is not α6-linked; or
   α3-linked to Glc-residue of a lactose residue to which NeuNAc is not α6-linked; and wherein said substance contains one fucose residue in the linear structure consisting of at least three lactosamine residues, or two fucose residues in the linear structure with two lactosamine residues and one lactose residue.

3. The method according to claim 1 or 2, wherein said oligosaccharide chain comprises a terminal NeuNAcα6 linked to three lactosamine residues.

4. The method according to claim 1 or 2, wherein the condition due to the presence of human influenza virus is a primary infection by an influenza virus in the respiratory tract.

5. The method according to claim 1 or 2, wherein the condition due to the presence of human influenza virus is a secondary bacterial infection.

6. The method according to claim 1 or 2, wherein a pharmaceutically effective amount of one or more additional substances effective against influenza viruses is administered.

7. The method according to claim 1 or 2, wherein said additional substance is a neuraminidase inhibitor.

8. A method for the treatment of a condition caused by human influenza virus, said method comprising administering a pharmaceutically effective amount of a substance to a patient in need thereof, wherein said substance comprises at least one oligosaccharide chain, said oligosaccharide chain comprising a terminal NeuNAcα6 linked to
   (a) a linear or branched polylactosamine type structure consisting of at least three lactosamine residues glycosidically linked to each other, wherein:
   when the structure is a linear structure, the structure contains optionally one or two fucose residues, each of which is α3-linked to a GlcNAc-residue of a lactosamine residue to which the terminal NeuNAc is not α6-linked; or
   when the structure is a branched structure, the structure optionally contains one or more additional NeuNAcα6 residues at a terminal position in a branch, and/or
   (b) a linear or branched structure consisting of two lactosamine and one lactose residue glycosidically linked to each other, wherein:
   when the structure is said linear type structure, the structure additionally contains one or two fucose residues, each of which is α3-linked to GlcNAc-residue of a lactosamine residue to which the terminal NeuNAc is not α6-linked; or
   α3-linked to Glc-residue of a lactose residue to which NeuNAc is not α6-linked; or
   when the structure is said branched structure, the structure optionally contains one or more additional NeuNAcα6 residues at a terminal position of the branch, wherein said substance contains an oligosaccharide structure of NeuNAcα6Galβ4GlcNAcβ3(NeuNAcα3/6Galβ4GlcNAcβ6)Galβ4GlcNAc/Glcβ1-, NeuNAcα6Galβ4GlcNAcβ3(NeuNAcα6Galβ4GlcNAcβ6)Galβ4GlcNAc/Glcβ1-, NeuNAcα6Galβ4GlcNAcβ3(Galβ4GlcNAcβ6)Galβ4GlcNAc/Glcβ1-, NeuNAcα6Galβ4GlcNAcβ3Galβ4GlcNAcβ3Galβ4(Fucα3)GlcNAcβ1-, or NeuNAcα6Galβ4GlcNAcβ3Galβ4(Fucα3)GlcNAcβ3Galβ4GlcNAcβ1.

9. A method for the treatment of a condition caused by human influenza virus, said method comprising administering a pharmaceutically effective amount of a substance to a patient in need thereof, wherein said substance comprises at least one oligosaccharide chain, said oligosaccharide chain comprising a terminal NeuNAcα6 linked to (a) a linear or branched polylactosamine type structure consisting of at least three lactosamine residues glycosidically linked to each other, wherein:

when the structure is a linear structure, the structure contains optionally one or two fucose residues, each of which is α3-linked to a GlcNAc-residue of a lactosamine residue to which the terminal NeuNAc is not α6-linked; or when the structure is a branched structure, the structure optionally contains one or more additional NeuNAcα6 residues at a terminal position in a branch, and/or (b) a linear or branched structure consisting of two lactosamine and one lactose residue glycosidically linked to each other, wherein:

when the structure is said linear type structure, the structure additionally contains one or two fucose residues, each of which is α3-linked to GlcNAc-residue of a lactosamine residue to which the terminal NeuNAc is not α6-linked; or α3-linked to Glc-residue of a lactose residue to which NeuNAc is not α6-linked; or when the structure is said branched structure, the structure optionally contains one or more additional NeuNAcα6 residues at a terminal position of the branch, wherein said oligosaccharide is a part of a glycolipid.

10. A method for the treatment of a condition caused by human influenza virus, said method comprising pharmaceutically effective amount of a substance to a patient in need thereof, wherein said substance comprises at least one oligosaccharide chain, said oligosaccharide chain comprising a terminal NeuNAcα6 linked to (a) a linear or branched polylactosamine type structure consisting of at least three lactosamine residues glycosidically linked to each other, wherein:

when the structure is a linear structure, the structure contains optionally one or two fucose residues, each of which is α3-linked to a GlcNAc-residue of a lactosamine residue to which the terminal NeuNAc is not α6-linked; or when the structure is a branched structure, the structure optionally contains one or more additional NeuNAcα6 residues at a terminal position in a branch, and/or (b) a linear or branched structure consisting of two lactosamine and one lactose residue glycosidically linked to each other, wherein:

when the structure is said linear type structure, the structure additionally contains one or two fucose residues, each of which is α3-linked to GlcNAc-residue of a lactosamine residue to which the terminal NeuNAc is not α6-linked; or α3-linked to Glc-residue of a lactose residue to which NeuNAc is not α6-linked; or when the structure is said branched structure, the structure optionally contains one or more additional NeuNAcα6 residues at a terminal position of the branch, said substance comprising at least two oligosaccharide chains.

* * * * *